United States Patent
Friedrichs et al.

(10) Patent No.: US 10,869,712 B2
(45) Date of Patent: Dec. 22, 2020

(54) SYSTEM AND METHOD FOR HIGH FREQUENCY LEAKAGE REDUCTION THROUGH SELECTIVE HARMONIC ELIMINATION IN ELECTROSURGICAL GENERATORS

(71) Applicants: COVIDIEN LP, Mansfield, MA (US); UNIVERSITY OF TENNESSEE RESEARCH FOUNDATION, Knoxville, TN (US)

(72) Inventors: Daniel A. Friedrichs, Aurora, CO (US); Mark A. Johnston, Boulder, CO (US); Daniel J. Costinett, Knoxville, TN (US); Bradford C. Trento, Knoxville, TN (US); Chongwen Zhao, Knoxville, TN (US)

(73) Assignee: Covidien LP, Mansfield, MA (US)

( * ) Notice: Subject to any disclaimer, the term of this patent is extended or adjusted under 35 U.S.C. 154(b) by 647 days.

(21) Appl. No.: 15/143,735

(22) Filed: May 2, 2016

(65) Prior Publication Data

US 2017/0312005 A1 Nov. 2, 2017

(51) Int. Cl.
A61B 18/12 (2006.01)
A61B 18/14 (2006.01)
(Continued)

(52) U.S. Cl.
CPC ...... *A61B 18/1206* (2013.01); *A61B 18/1445* (2013.01); *A61B 17/29* (2013.01);
(Continued)

(58) Field of Classification Search
CPC ........... A61B 2018/00636; A61B 2018/00642; A61B 2018/00702; A61B 2018/00708;
(Continued)

(56) References Cited

U.S. PATENT DOCUMENTS 6,193,713 B1 2/2001 Geistert et al.
D574,323 S 8/2008 Waaler
(Continued)

FOREIGN PATENT DOCUMENTS

DE 179607 C 3/1905
DE 390937 C 3/1924
(Continued)

OTHER PUBLICATIONS

Wald et al., "Accidental Burns", JAMA, Aug. 16, 1971, vol. 217, No. 7, pp. 916-921.
(Continued)

*Primary Examiner* — Jaymi E Della
*Assistant Examiner* — Sean W Collins
(74) *Attorney, Agent, or Firm* — Carter, DeLuca & Farrell LLP (57) ABSTRACT

An electrosurgical generator includes: a power supply configured to output a DC waveform; an inverter coupled to the power supply, the inverter including a plurality of switching elements; and a controller coupled to the inverter and configured to generate a switching angle waveform including a plurality of switching pulses. The controller is further configured to at least one of select or calculate the plurality of switching pulses to activate the plurality of switching elements to generate a radio frequency waveform based on the DC waveform and to minimize harmonics of the radio frequency waveform.

12 Claims, 6 Drawing Sheets

(51) Int. Cl.
  *A61B 18/00* (2006.01)
  *A61B 17/29* (2006.01)
(52) U.S. Cl.
  CPC ............... *A61B 2017/2948* (2013.01); *A61B 2018/00994* (2013.01); *A61B 2018/1266* (2013.01)
(58) Field of Classification Search
  CPC .. A61B 2018/0072; A61B 2018/00726; A61B 2018/00732; A61B 2018/0075; A61B 2018/00761; A61B 2018/00851; A61B 2018/00857; A61B 2018/1293; A61B 18/1206; A61B 18/1233; A61B 18/1445; A61B 2018/1266; A61B 2018/00994; A61B 2017/2948; A61B 17/29
  See application file for complete search history.

(56) References Cited

U.S. PATENT DOCUMENTS

| | | | |
|---|---|---|---|
| 8,998,939 B2 | 4/2015 | Price et al. | |
| 9,099,863 B2 | 8/2015 | Smith et al. | |
| 9,186,202 B2 | 11/2015 | Gilbert | |
| 9,192,423 B2 | 11/2015 | Schall et al. | |
| 9,270,202 B2 | 2/2016 | Johnson et al. | |
| 9,283,028 B2 | 3/2016 | Johnson | |
| 2004/0097914 A1* | 5/2004 | Pantera | A61B 18/1206 606/34 |
| 2004/0167508 A1 | 8/2004 | Wham et al. | |
| 2004/0186470 A1* | 9/2004 | Goble | A61B 18/042 606/41 |
| 2009/0062786 A1* | 3/2009 | Garito | A61B 18/12 606/37 |
| 2010/0137854 A1 | 6/2010 | Hosier | |
| 2013/0305760 A1* | 11/2013 | Shinomoto | F25B 49/025 62/238.7 |
| 2013/0325380 A1 | 12/2013 | Behnke, II et al. | |
| 2014/0029152 A1 | 1/2014 | Mazzola et al. | |
| 2014/0232463 A1 | 8/2014 | Gilbert | |
| 2014/0243815 A1 | 8/2014 | Kerr | |
| 2014/0253140 A1 | 9/2014 | Gilbert | |
| 2014/0257270 A1 | 9/2014 | Behnke | |
| 2014/0258800 A1 | 9/2014 | Gilbert | |
| 2014/0276750 A1 | 9/2014 | Gilbert | |
| 2014/0276753 A1 | 9/2014 | Wham et al. | |
| 2014/0276754 A1 | 9/2014 | Gilbert et al. | |
| 2014/0358138 A1 | 12/2014 | Mattmiller et al. | |
| 2014/0376269 A1 | 12/2014 | Johnson et al. | |
| 2015/0025521 A1 | 1/2015 | Friedrichs et al. | |
| 2015/0025523 A1 | 1/2015 | Friedrichs et al. | |
| 2015/0032096 A1 | 1/2015 | Johnson | |
| 2015/0032098 A1 | 1/2015 | Larson et al. | |
| 2015/0032099 A1 | 1/2015 | Larson et al. | |
| 2015/0032100 A1 | 1/2015 | Coulson et al. | |
| 2015/0088116 A1 | 3/2015 | Wham | |
| 2015/0088117 A1 | 3/2015 | Gilbert et al. | |
| 2015/0088118 A1 | 3/2015 | Gilbert et al. | |
| 2015/0088124 A1 | 3/2015 | Wham | |
| 2015/0088125 A1 | 3/2015 | Wham | |
| 2015/0119871 A1 | 4/2015 | Johnson et al. | |
| 2015/0223865 A1 | 8/2015 | Krapohl et al. | |
| 2015/0357938 A1* | 12/2015 | Yamasaki | H02P 27/00 363/41 |
| 2016/0074091 A1 | 3/2016 | Amoah et al. | |
| 2017/0302154 A1* | 10/2017 | Tada | H02M 1/08 |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2602517 A1 | 7/1976 |
| DE | 2504280 A1 | 8/1976 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3904558 A1 | 8/1990 |
| DE | 3942998 A1 | 7/1991 |
| DE | 4206443 A1 | 9/1993 |
| DE | 4339049 A1 | 5/1995 |
| DE | 19506363 A1 | 8/1996 |
| DE | 19717411 A1 | 11/1998 |
| DE | 19848540 A1 | 5/2000 |
| DE | 10 2008058737 A1 | 4/2010 |
| EP | 0 246 350 A1 | 11/1987 |
| EP | 267403 A2 | 5/1988 |
| EP | 296777 A2 | 12/1988 |
| EP | 310431 A2 | 4/1989 |
| EP | 325456 A2 | 7/1989 |
| EP | 336742 A2 | 10/1989 |
| EP | 390937 A1 | 10/1990 |
| EP | 0 556 705 A1 | 8/1993 |
| EP | 608609 A2 | 8/1994 |
| EP | 0 836 868 A2 | 4/1998 |
| EP | 880220 A2 | 11/1998 |
| EP | 0 882 955 A1 | 12/1998 |
| EP | 1051948 A2 | 11/2000 |
| EP | 1366724 A1 | 12/2003 |
| EP | 1776929 A1 | 4/2007 |
| EP | 2829248 A1 | 1/2015 |
| FR | 1 275 415 A | 11/1961 |
| FR | 1 347 865 A | 1/1964 |
| FR | 2 313 708 A1 | 12/1976 |
| FR | 2364461 A1 | 4/1978 |
| FR | 2 502 935 A1 | 10/1982 |
| FR | 2 517 953 A1 | 6/1983 |
| FR | 2 573 301 A1 | 5/1986 |
| JP | 63 005876 A | 1/1988 |
| JP | 2002-065690 A | 3/2002 |
| JP | 2005-185657 A | 7/2005 |
| JP | 2013512056 A | 4/2013 |
| JP | 2014500058 A | 1/2014 |
| SU | 166452 | 1/1965 |
| SU | 727201 A2 | 4/1980 |
| WO | 02/11634 A1 | 2/2002 |
| WO | 02/45589 A2 | 6/2002 |
| WO | 03/090635 A1 | 11/2003 |
| WO | 06/050888 A1 | 5/2006 |
| WO | 08/053532 A1 | 5/2008 |
| WO | 2015094749 A1 | 6/2015 |

OTHER PUBLICATIONS

Vallfors et al., "Automatically Controlled Bipolar Electrosoagulation-'COA-COMP'", Neurosurgical Review 7:2-3 (1984) pp. 187-190.
Sugita et al., "Bipolar Coagulator with Automatic Thermocontrol", J. Neurosurg., vol. 41, Dec. 1944, pp. 777-779.
Prutchi et al. "Design and Development of Medical Electronic Instrumentation", John Wiley & Sons, Inc. 2005.
Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.
Muller et al. "Extended Left Hemicolectomy Using the LigaSure Vessel Sealing System", Innovations That Work; Company Newsletter; Sep. 1999.
"Electrosurgical Unit Analyzer ESU-2400 Series User Manual" Apr. 1, 2002; Retrieved from Internet: <URL:http://www.bcgroupintl.com/ESU_2400/Updates/ESU-2400_UM_Rev04.pdf>, pp. 6, 11, 73.

(56) References Cited

OTHER PUBLICATIONS

Ogden Goertzel Alternative to the Fourier Transform: Jun. 1993 pp. 485-487, Electronics World; Reed Business Publishing, Sutton, Surrey, BG vol. 99, No. 9. 1687.
Hadley I C D et al., "Inexpensive Digital Thermometer for Measurements on Semiconductors", International Journal of Electronics; Taylor and Francis. Ltd.; London, GB; vol. 70, No. 6 Jun. 1, 1991; pp. 1155-1162.
Richard Wolf Medical Instruments Corp. Brochure, "Kleppinger Bipolar Forceps & Bipolar Generator", 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.
Geddes et al., "The Measurement of Physiologic Events by Electrical Impedence", Am. J. MI, Jan. Mar. 1964, pp. 16-27.
Rosman et al., "Methods of Making Nervous System Lesions", In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Rosman et al., "Radiofrequency Lesion Generation and Its Effect on Tissue Impedance", Applied Neurophysiology 51: (1988) pp. 230-242.
Zlatanovic M., "Sensors in Diffusion Plasma Processing" Microelectronics 1995; Proceedings 1995; 20th International Conference CE on Nis, Serbia Sep. 12-14, 1995; New York, NY vol. 2 pp. 565-570.
Ni W. et al. "A Signal Processing Method for the Coriolis Mass Flowmeter Based on a Normalized . . . ", Journal of Applied Sciences-Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297, Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Rosman et al., "Theoretical Aspects of Radiofrequency Lesions in the Dorsal Root Entry Zone", Neurosurgery 15: (1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300", 1 p. Sep. 1998.
Valleylab Brochure "Valleylab Electroshield Monitoring System", 2 pp. Nov. 1995.
U.S. Appl. No. 10/406,690 dated Apr. 3, 2003 inventor: Behnke.
U.S. Appl. No. 10/573,713 dated Mar. 28, 2006 inventor: Wham.
U.S. Appl. No. 11/242,458 dated Oct. 3, 2005 inventor: Becker.
Japanese Notice of Allowance dated Aug. 20, 2018 issued in corresponding JP Appln. No. 2017-007701. (Summary only).
European Search Report dated Nov. 3, 2017 issued in corresponding European Application No. 17168913.8.
Extended European Search Report dated Nov. 27, 2018 issued in corresponding EP Appln. No. 18193703.8.
Chinese Office Action dated May 14, 2019 issued in corresponding CN Appln. No. 201710287389.6. (Summary Only).

\* cited by examiner

SYSTEM AND METHOD FOR HIGH FREQUENCY LEAKAGE REDUCTION THROUGH SELECTIVE HARMONIC ELIMINATION IN ELECTROSURGICAL GENERATORS

BACKGROUND

Technical Field

The present disclosure relates to systems and methods for eliminating or minimizing leakage current in an electrosurgical generator. In particular, the present disclosure relates to an electrosurgical generator configured to reduce the amplitude of high frequency harmonic waveforms, which cause leakage current, using selective harmonic elimination modulation.

Background of Related Art

Electrosurgery involves application of high radio frequency ("RF") electrical current to a surgical site to cut, ablate, desiccate, or coagulate tissue. In monopolar electrosurgery, a source or active electrode delivers radio frequency alternating current from the electrosurgical generator to the targeted tissue. A patient return electrode is placed remotely from the active electrode to conduct the current back to the generator.

In bipolar electrosurgery, return and active electrodes are placed in close proximity to each other such that an electrical circuit is formed between the two electrodes (e.g., in the case of an electrosurgical forceps). In this manner, the applied electrical current is limited to the body tissue positioned between the electrodes. Accordingly, bipolar electrosurgery generally involves the use of instruments where it is desired to achieve a focused delivery of electrosurgical energy between two electrodes positioned on the instrument, e.g. forceps or the like.

During use, high frequency currents may leak from the electrosurgical generators through parasitic circuit pathways due to stray capacitance between components of the electrosurgical generator. Accordingly, there is a need to for electrosurgical generators that limit leakage current. However, conventional electrosurgical generators utilize leakage mitigation circuits, such as leakage chokes, harmonic filters, and low parasitic capacitance components. These circuits are costly and require significant engineering to be properly implemented within electrosurgical generators. Accordingly, there is a need for electrosurgical generators that minimize leakage current without the need for conventional leakage mitigation circuits.

SUMMARY

The present disclosure provides an electrosurgical generator including a non-resonant power converter having one or more switching elements controlled by a switching waveform (e.g., a pulse-width modulated waveform) generated by a controller. The switching waveform is calculated using a selective harmonic elimination algorithm to reduce and/or eliminate the amplitude of high-frequency harmonics present in an RF waveform generated by the non-resonant power converter. Higher frequency harmonic waveforms encounter lower impedance through parasitic leakage paths, hence, these waveforms leak more readily than the fundamental or lower harmonic waveforms. Thus, by reducing the amplitude of higher frequency waveforms, the electrosurgical generator according to the present disclosure dramatically reduces total leakage current without affecting power delivered at the fundamental frequency.

According to an embodiment of the present disclosure, an electrosurgical generator is disclosed. The electrosurgical generator includes: a power supply configured to output a DC waveform and an inverter coupled to the power supply and including a plurality of switching elements. The electrosurgical generator also includes a controller coupled to the inverter and configured to generate a switching angle waveform including a plurality of switching pulses. The controller is further configured to select or calculate the plurality of switching pulses to activate the plurality of switching elements to generate a radio frequency waveform based on the DC waveform and to minimize harmonics of the radio frequency waveform.

According to another embodiment of the present disclosure, an electrosurgical system is disclosed. The electrosurgical system includes an electrosurgical generator, which includes a power supply configured to output a DC waveform and an inverter coupled to the power supply and including a plurality of switching elements. The electrosurgical generator also includes a controller coupled to the inverter and configured to generate a switching angle waveform including a plurality of switching pulses. The controller is further configured to select or calculate the plurality of switching pulses to activate the plurality of switching elements to generate a radio frequency waveform based on the DC waveform and to minimize harmonics of the radio frequency waveform. The electrosurgical system also includes an electrosurgical instrument configured to couple to the inverter and to transmit the radio frequency waveform.

According to one aspect of any of the above embodiments, the controller is further configured to vary a switching frequency and a duty cycle of the switching angle waveform. The controller may be further configured to generate five switching pulses per each half period of the radio frequency waveform.

According to another aspect of any of the above embodiments, the inverter includes four switching elements arranged in an H-bridge topology. Each of the switching elements is a wide bandgap field effect transistor.

According to another aspect of any of the above embodiments, the switching angle waveform is a unipolar symmetrical waveform or a bipolar symmetrical waveform.

BRIEF DESCRIPTION OF THE DRAWINGS

The present disclosure may be understood by reference to the accompanying drawings, when considered in conjunction with the subsequent, detailed description, in which.

DETAILED DESCRIPTION

Particular embodiments of the present disclosure will be described below with reference to the accompanying drawings. In the following description, well-known functions or constructions are not described in detail to avoid obscuring the present disclosure in unnecessary detail. Those skilled in the art will understand that the present disclosure may be adapted for use with any electrosurgical instrument. It should also be appreciated that different electrical and mechanical connections and other considerations may apply to each particular type of instrument.

A generator according to the present disclosure can operate ultrasonic and electrosurgical instruments at multiple frequencies. In particular, the generator may be used in monopolar and/or bipolar electrosurgical procedures, including, for example, cutting, coagulation, ablation, and vessel sealing procedures. The generator may include a plurality of outputs for interfacing with various ultrasonic and electrosurgical instruments (e.g., ultrasonic dissectors and hemostats, monopolar instruments, return electrode pads, bipolar electrosurgical forceps, footswitches, etc.). Further, the generator includes electronic circuitry configured to generate radio frequency energy specifically suited for powering ultrasonic instruments and electrosurgical devices operating in various electrosurgical modes (e.g., cut, blend, coagulate, division with hemostasis, fulgurate, spray, etc.) and procedures (e.g., monopolar, bipolar, vessel sealing).

Figure 1:
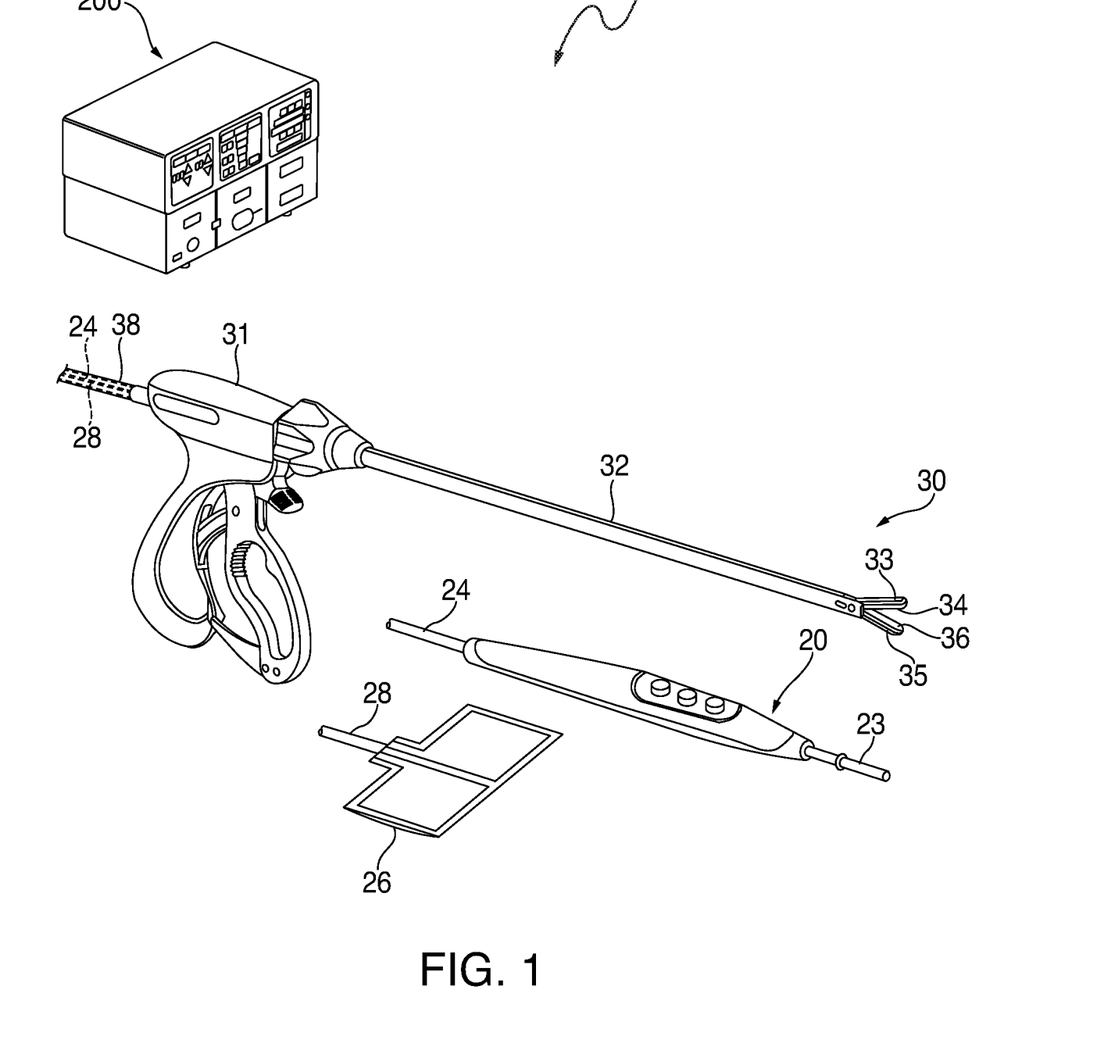
FIG. 1 is a perspective view of a surgical system according to an embodiment of the present disclosure.

FIG. 1 is a perspective view of the components of one illustrative embodiment of an electrosurgical system 10 according to the present disclosure. The system 10 may include one or more monopolar electrosurgical instruments 20 having one or more active electrodes 23 (e.g., electrosurgical cutting probe, ablation electrode(s), etc.) for treating tissue of a patient. Electrosurgical alternating RF current is supplied to the instrument 20 by a generator 200 via a supply line 24 that is connected to an active terminal 230 (FIG. 3) of the generator 200, allowing the instrument 20 to cut, coagulate, thermally or non-thermally ablate and/or otherwise treat tissue. The alternating RF current is returned to the generator 200 through a return electrode pad 26 via a return line 28 at a return terminal 232 (FIG. 3) of the generator 200. For monopolar operation, the system 10 may include a plurality of return electrode pads 26 that, in use, are disposed on a patient to minimize the chances of tissue damage by maximizing the overall contact area with the patient. In addition, the generator 200 and the return electrode pads 26 may be configured for monitoring tissue-to-patient contact to ensure that sufficient contact exists therebetween.

Figure 3:
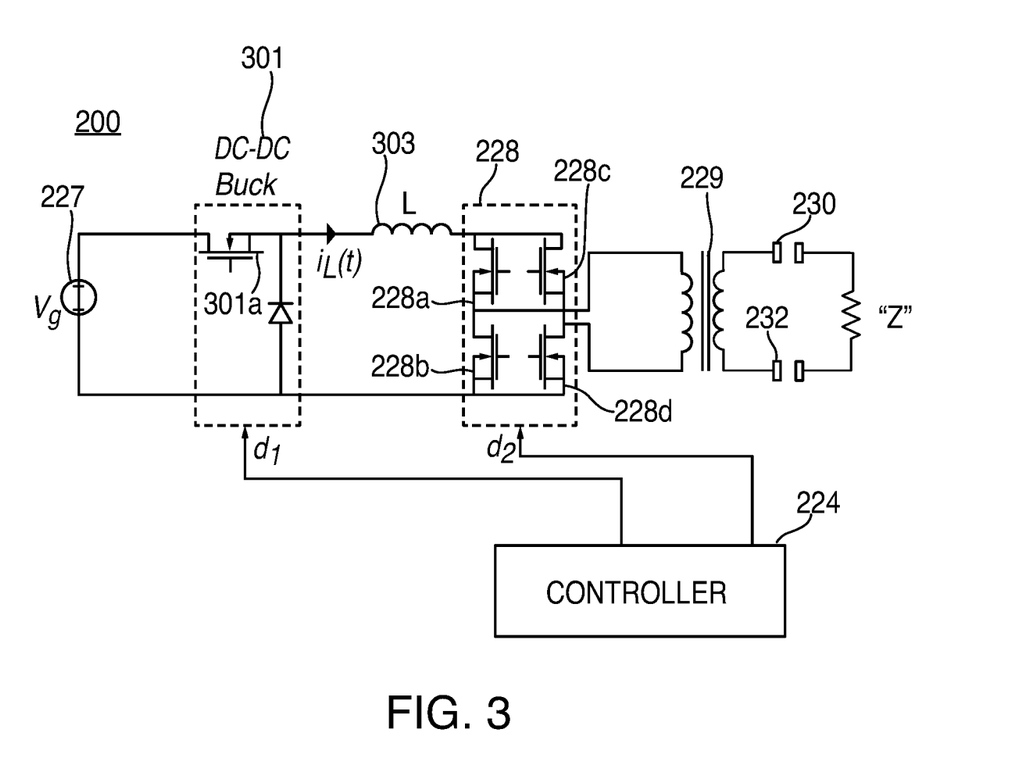
FIG. 3 is a schematic diagram of the electrosurgical generator of FIG. 2 according to an embodiment of the present disclosure.

The system 10 may also include one or more bipolar electrosurgical instruments, for example, a bipolar electrosurgical forceps 30 having one or more electrodes for treating tissue of a patient. The electrosurgical forceps 30 includes a housing 31 and opposing jaw members 33 and 35 disposed at a distal end of a shaft 32. The jaw members 33 and 35 have one or more active electrodes 34 and a return electrode 36 disposed therein, respectively. The active electrode 34 and the return electrode 36 are connected to the generator 200 through cable 38 that includes the supply and return lines 24, 28, which may be coupled to the active and return terminals 230, 232, respectively (FIG. 3). The electrosurgical forceps 30 is coupled to the generator 200 at a port having connections to the active and return terminals 230 and 232 (e.g., pins) via a plug (not shown) disposed at the end of the cable 38, wherein the plug includes contacts from the supply and return lines 24, 28 as described in more detail below.

Figure 2:
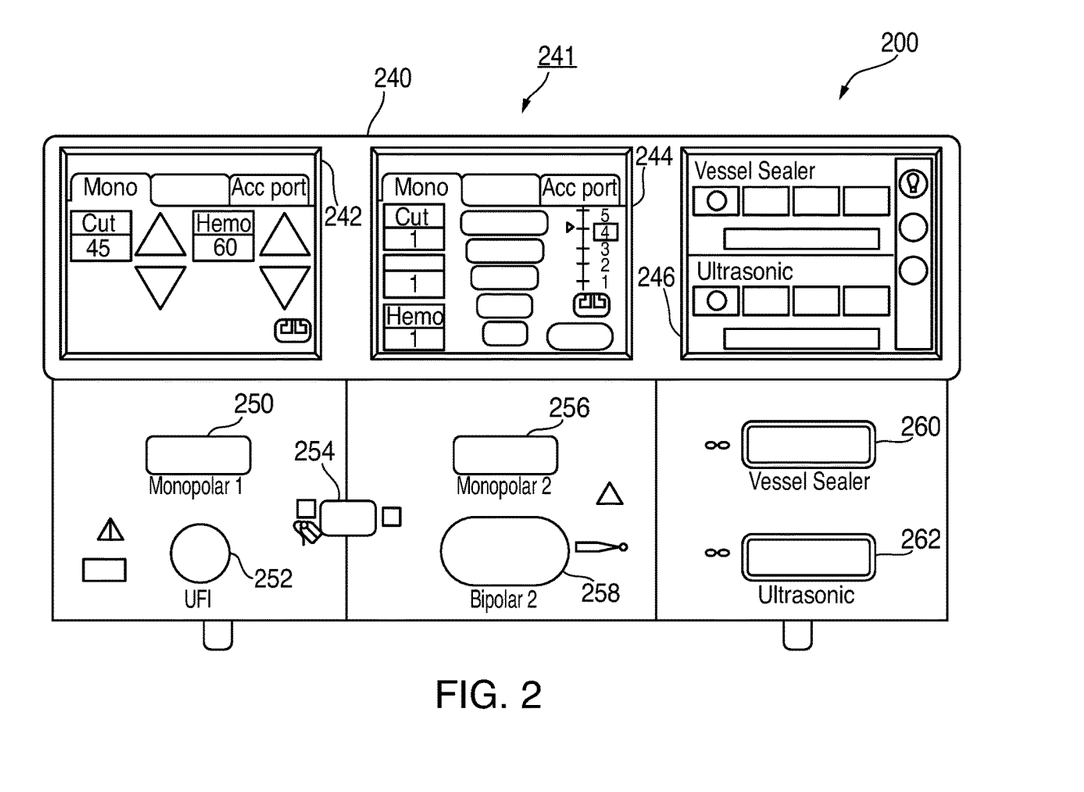
FIG. 2 is a front view of an electrosurgical generator of FIG. 1 according to an embodiment of the present disclosure.

With reference to FIG. 2, a front face 240 of the generator 200 is shown. The generator 200 may include a plurality of ports 250-262 to accommodate various types of electrosurgical instruments (e.g., monopolar electrosurgical instrument 20, electrosurgical forceps 30, etc.).

The generator 200 includes a user interface 241 having one or more display screens 242, 244, 246 for providing the user with variety of output information (e.g., intensity settings, treatment complete indicators, etc.). Each of the screens 242, 244, 246 is associated with a corresponding port 250-262. The generator 200 includes suitable input controls (e.g., buttons, activators, switches, touch screen, etc.) for controlling the generator 200. The screens 242, 244, 246 are also configured as touch screens that display a corresponding menu for the instruments (e.g., electrosurgical forceps 30, etc.). The user then adjusts inputs by simply touching corresponding menu options.

Screen 242 controls monopolar output and the devices connected to the ports 250 and 252. Port 250 is configured to couple to a monopolar electrosurgical instrument (e.g., electrosurgical instrument 20) and port 252 is configured to couple to a foot switch (not shown). The foot switch may be used to provide for additional inputs (e.g., replicating inputs of the generator 200). Screen 244 controls monopolar and bipolar output and the devices connected to the ports 256 and 258. Port 256 is configured to couple to other monopolar instruments. Port 258 is configured to couple to a bipolar instrument (not shown).

Screen 246 controls the electrosurgical forceps 30 that may be plugged into one of the ports 260 and 262, respectively. The generator 200 outputs energy through the ports 260 and 262 suitable for sealing tissue grasped by the electrosurgical forceps 30. In particular, screen 246 outputs a user interface that allows the user to input a user-defined intensity setting for each of the ports 260 and 262. The user-defined setting may be any setting that allows the user to adjust one or more energy delivery parameters, such as power, current, voltage, energy, etc. or sealing parameters, such as energy rate limiters, sealing duration, etc. The user-defined setting is transmitted to a controller 224 (FIG. 3) where the setting may be saved in memory. In embodiments, the intensity setting may be a number scale, such as for example, from one to ten or one to five. In embodiments, the intensity setting may be associated with an output curve of the generator 200. The intensity settings may be specific for each electrosurgical forceps 30 being utilized, such that various instruments provide the user with a specific intensity scale corresponding to the electrosurgical forceps 30. The active and return terminals 230 and 232 (FIG. 3) may be coupled to any of the desired ports 250-262. In embodiments, the active and return terminals 230 and 232 may be coupled to the ports 250-262.

FIG. 3 shows a schematic block diagram of the generator 200, which includes a controller 224, a power supply 227, and a power converter 228. The power supply 227 may be a high voltage, DC power supply connected to an AC source (e.g., line voltage) and provides high voltage, DC power to the power converter 228, which then converts high voltage, DC power into RF energy and delivers the energy to the active terminal 230. The energy is returned thereto via the return terminal 232. In particular, electrosurgical energy for energizing the monopolar electrosurgical instrument 20 and/or electrosurgical forceps 30 is delivered through the active and return terminals 230 and 232. The active and return terminals 230 and 232 are coupled to the power converter 228 through an isolation transformer 229.

The generator 200 also includes a DC-DC buck converter 301 coupled to the power supply 227. Furthermore, a current source 303, e.g., an inductor, is electrically coupled to the DC-DC buck converter 301 and the power converter 228. The current source 303 may be an inductor having a relatively large inductance which smoothes the current supplied to the power converter 228. The current source 303 is configured to supply relatively constant current to the power converter 228. The output of power converter 228 transmits current through an isolation transformer 229 to the load "Z", e.g., tissue being treated.

The power converter 228 is configured to operate in a plurality of modes, during which the generator 200 outputs corresponding waveforms having specific duty cycles, peak voltages, crest factors, etc. It is envisioned that in other embodiments, the generator 200 may be based on other types of suitable power supply topologies. Power converter 228 may be a resonant RF amplifier or a non-resonant RF amplifier, as shown. A non-resonant RF amplifier, as used herein, denotes an amplifier lacking any tuning components, i.e., conductors, capacitors, etc., disposed between the power converter and the load "Z."

The controller 224 includes a processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to perform the calculations and/or set of instructions described herein.

The controller 224 includes an output port that is operably connected to the power supply 227 and/or power converter 228 allowing the processor to control the output of the generator 200 according to either open and/or closed control loop schemes. A closed loop control scheme is a feedback control loop, in which a plurality of sensors measure a variety of tissue and energy properties (e.g., tissue impedance, tissue temperature, output power, current and/or voltage, etc.), and provide feedback to the controller 224. The controller 224 then controls the power supply 227 and/or power converter 228, which adjusts the DC and/or power supply, respectively.

The generator 200 according to the present disclosure may also include a plurality of sensors (not shown). The sensors may be coupled to the power supply 227, DC-DC buck converter 301, the current source 303, and/or power converter 228 and may be configured to sense properties of DC current supplied to the power converter 228 and/or RF energy outputted by the power converter 228, respectively. Various components of the generator 200, namely, the power converter 228 and the current and voltage sensors, may be disposed on a printed circuit board (PCB). The controller 224 also receives input signals from the input controls of the generator 200, the instrument 20, and/or electrosurgical forceps 30. The controller 224 utilizes the input signals to adjust power outputted by the generator 200 and/or performs other control functions thereon.

The DC-DC buck converter 301 includes a switching element 301a and power converter 228 includes a plurality of switching elements 228a-228d arranged in an H-bridge topology. In embodiments, power converter 228 may be configured according to any suitable topology including, but not limited to, half-bridge, full-bridge, push-pull, and the like. Suitable switching elements include voltage-controlled devices such as transistors, field-effect transistors (FETs), combinations thereof, and the like. In embodiments, the FETs may be formed from gallium nitride, aluminum nitride, boron nitride, silicone carbide, or any other suitable wide bandgap materials.

The controller 224 is in communication with both DC-DC buck converter 301 and power converter 228, in particular, the switching elements 301a and 228a-228d, respectively. Controller 224 is configured to output control signals, which may be a pulse-width modulated ("PWM") signal, to switching elements 301a and 228a-228d as described in further detail in co-pending application published as US 2014/0254221, the entire contents of which are incorporated by reference herein. In particular, controller 224 is configured to modulate a control signal $d_1$ supplied to switching element 301a of DC-DC buck converter 301 and control signal $d_2$ supplied to switching elements 228a-228d of power converter 228. Additionally, controller 224 is configured to calculate power characteristics of generator 200, and control generator 200 based at least in part on the measured power characteristics including, but not limited to, current passing through the inductor 303, DC output of the DC-DC buck converter 301, and the voltage and current at the output of power converter 228.

The generator 200 according to the present disclosure, and in particular, the controller 224 is configured to operate the power converter 228 using a selective harmonic elimination ("SHE") modulation method. Moreover, the SHE modulation according to the present disclosure is applicable to a variety of DC/AC topologies, such as half-bridge, full bridge, multilevel inverter, and resonant type inverters and the power converter 228 is an exemplary embodiment. In SHE modulation, the controller 200 signals the power converter 228 to generate a radio frequency waveform at a fundamental frequency, while diminishing undesired higher harmonics. In particular, the controller 224 is configured to generate PWM control signals to the switching elements 228a-228d as a switching angle waveform. Each of the switching angle waveforms is based on switching angles for each of the switching elements 228a-228d, which when activated, generate an RF waveform for energizing the electrosurgical instruments connected to the generator 200, such as the monopolar electrosurgical instrument 20 or the electrosurgical forceps 30.

Figure 4:
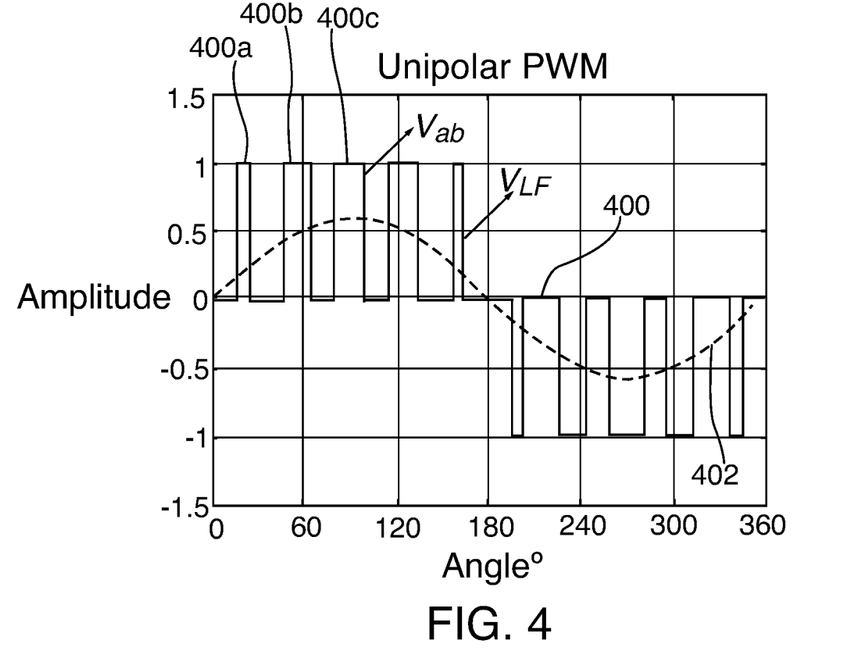
FIG. 4 is a plot of a unipolar switching angle waveform and a radio frequency waveform according to an embodiment of the present disclosure.
Figure 5:
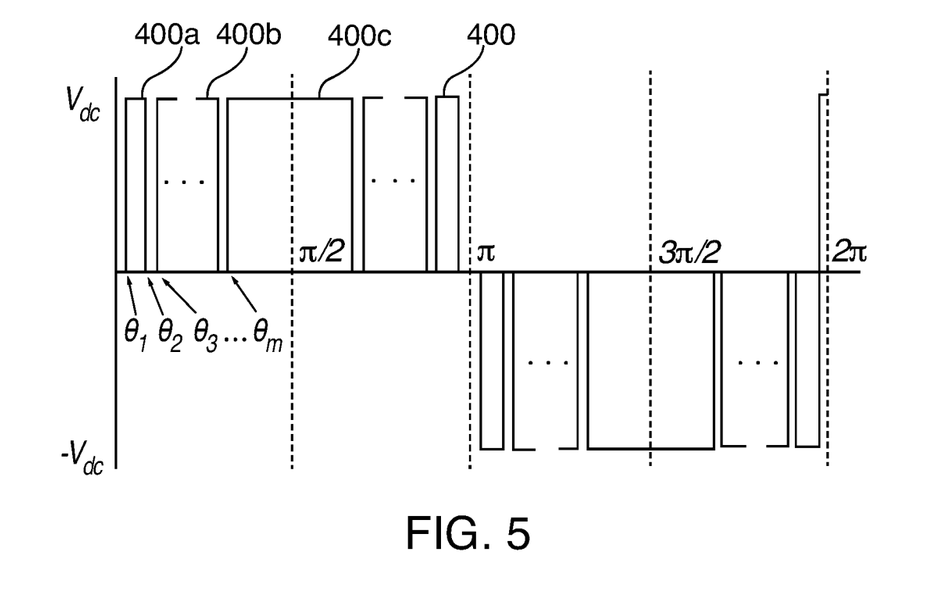
FIG. 5 is a radian plot of the unipolar switching angle waveform of FIG. 4 according to the present disclosure.

With reference to FIG. 4, an exemplary switching angle waveform and a resulting RF waveform are shown. FIGS. 4 and 5 show a quarter symmetric, unipolar switching angle waveform 400 for generating a sinusoidal RF waveform 402 (FIG. 4). The term "unipolar" as used herein denotes a waveform having switching pulses that oscillate between 0 and either positive ($V_{dc}$) or negative ($-V_{dc}$) voltage as shown in FIG. 5. The unipolar switching angle waveform 400 includes a plurality of pulses 400a, b, c, . . . n corresponding to the switching angles for each of the switching elements 228a-228d (FIG. 3).

All of the positive and negative cycles of the unipolar switching angle waveform 400 produce the positive and negative cycles of the RF waveform 402, respectively. In particular, there are multiple switching pulses 400a, b, c, . . . n of varying duration per period of the RF waveform 402. The term "period" as used herein denotes the time it takes to complete one full cycle of a waveform. Thus, for each period of the RF waveform 402, there are ten (10) switching pulses 400a, b, c, . . . n and five (5) per half cycle/period. In addition, the switching pulses 400a, b, c, . . . n are of different duration based on the SHE algorithm as described in further detail below. With reference to FIG. 5, the switching pulses 400a, 400b, and 400c are of different duration and are symmetrical about quarter cycle/period ($\pi/2$). Each of the pulses 400a, b, c, . . . n be calculated by the controller 224 are based on a desired frequency of the RF waveform 402.

Figure 6:
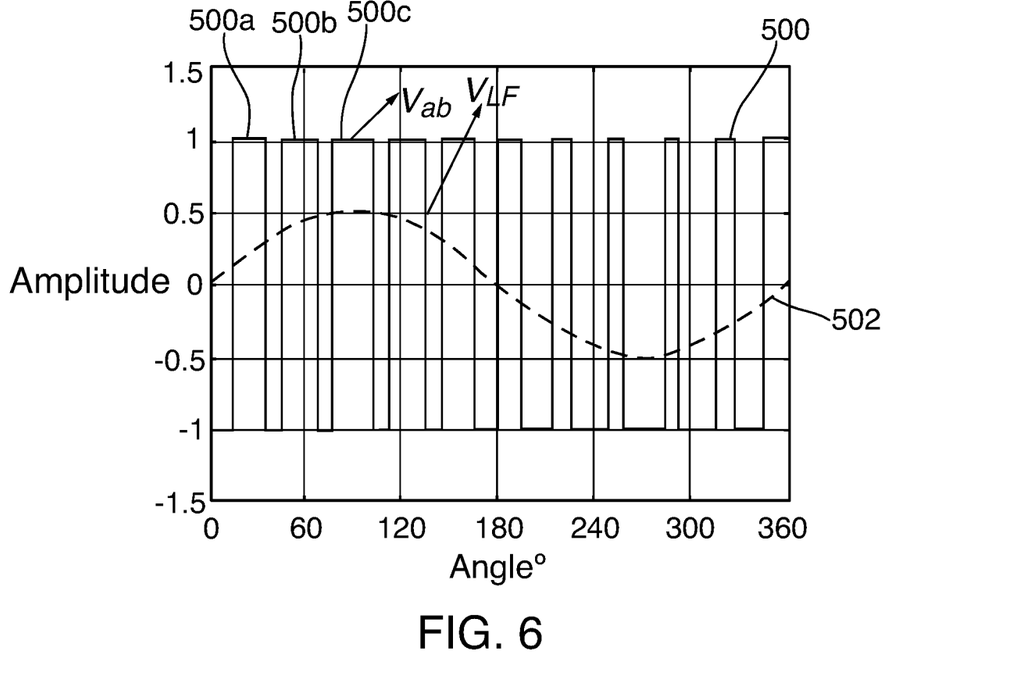
FIG. 6 is a plot of a bipolar switching angle waveform and a radio frequency waveform according to an embodiment of the present disclosure.
Figure 7:
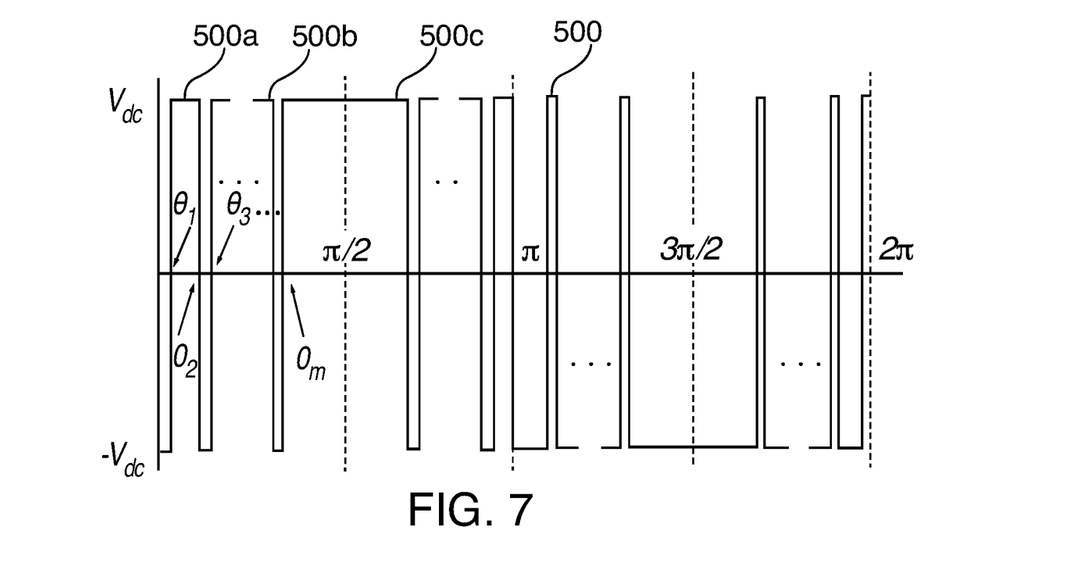
FIG. 7 is a radian plot of the bipolar switching angle waveform of FIG. 6 according to an embodiment of the present disclosure.

FIGS. 6 and 7 show a quarter symmetric, bipolar switching angle waveform 500 for generating a sinusoidal RF waveform 502, which is substantially similar to the sinusoidal RF waveform 402. The term "bipolar" as used herein denotes a waveform having switching pulses that oscillate between positive ($V_{dc}$) and negative ($-V_{dc}$) voltages as shown in FIG. 7. The bipolar switching angle waveform 500 includes a plurality of pulses 500a, b, c, . . . n corresponding to the switching angles for each of the switching elements 228a-228d (FIG. 3). The pulses of the switching angle waveform 500 also correspond to the positive and negative cycles of the RF waveform 502.

All of the positive and negative cycles of the bipolar switching angle waveform 500 produce the positive and negative cycles of the RF waveform 502. In particular, there are multiple switching pulses 500a, b, c, . . . n of varying duration per period of the RF waveform 502. Thus, for each period of the RF waveform 502, there are ten (10) switching pulses 500a, b, c, . . . n, and five (5) per half cycle/period. With reference to FIG. 7, the switching pulses 500a, 500b, and 500c are of different duration and are symmetrical about quarter cycle/period ($\pi/2$). The pulses may be calculated by the controller 224 based on a desired frequencies of the RF waveform 502.

Frequencies of each of the RF waveforms 402, 502 may be set by a user using the user interface 241 (FIG. 2). The controller 224 may then calculate the switching angles for generating the waveforms 402 and 502. In particular, the controller 224 may calculate the number, frequency, and duration of the switching angles, e.g., duration of the pulses 400a, b, c, . . . n and 500a, b, c, . . . n. In embodiments, these properties may be calculated offline either by the controller 224 or any other suitable processor.

Figure 8:
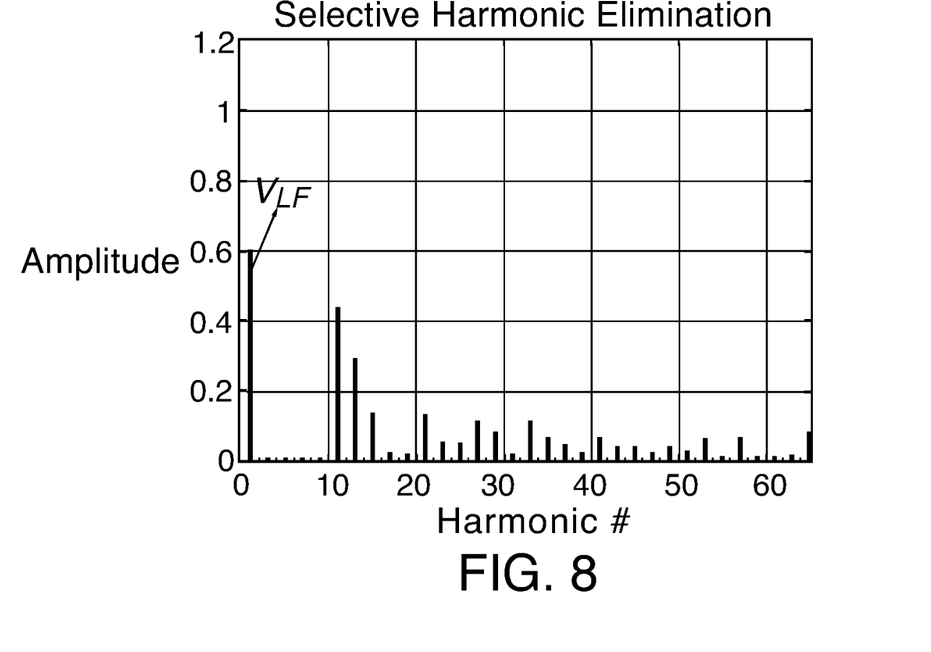
FIG. 8 is a bar graph of a frequency domain spectrum of the radio frequency waveform generated by the unipolar switching angle waveform of FIG. 4.
Figure 9:
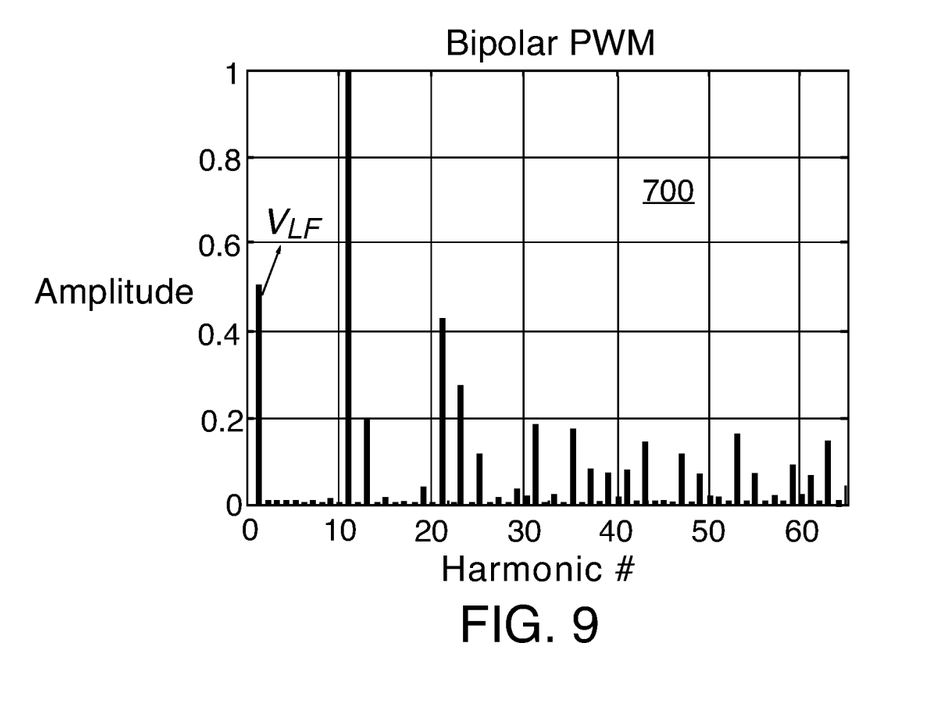
FIG. 9 is a bar graph of a frequency domain spectrum of the radio frequency waveform generated by the bipolar switching angle waveform of FIG. 6.

FIGS. 8 and 9 show harmonic frequency plots 600 and 700 generated by the switching angle waveforms 400 and 500, respectively. The plots 600 and 700 are bar graphs illustrating the frequency domain spectrum of the RF waveforms 402 and 502, respectively, including the number of harmonics and their amplitude. The fundamental frequency waveform is shown as the first bar in each of the plots 600 and 700 and represents the RF waveform 402 and 502, respectively. The plots 600 and 700 also show that the SHE modulation method eliminates and/or decreases all of the harmonic waveforms as illustrated by the lower amplitude of the harmonic waveforms with respect to the fundamental waveform.

To eliminate undesired harmonics of the RF waveforms 402 and 502, the present disclosure utilizes a SHE modulation method, which allows for fundamental and certain harmonics to be independently controlled. This also allows for individual power regulation and elimination of undesired harmonics, which reduces leakage current, energy losses, and electro-magnetic interference. Compared to traditional PWM modulation, which controls only the fundamental frequency of the output waveform through modulation of duty cycle at constant frequency, SHE modulation varies both switching frequency and duty cycle per switching period in order to generate an output in which a large range of the output spectrum is directly controlled. The SHE method according to the present disclosure uses Fourier analysis, based on the desired output spectrum, to synthesize a switching angle waveform e.g., a pulse train, having a plurality of discrete switching pulses/periods.

The pulses 400a, b, c, . . . n of the quarter symmetric, unipolar switching angle waveform 400 are calculated using SHE algorithm according to the present disclosure. The algorithm may be a root-finding algorithm, which iterates a plurality of times to calculate a root of the non-linear equations illustrated in formulas (1)-(4) below. Fourier expansion of the switching angle waveform 400 may be done using the formula (1) below:

$$v(\omega t) = \sum_{n=1,3,5,...}^{\infty} \frac{4V_{dc}}{n\pi}[\cos(n\theta_1) - \cos(n\theta_2) + \cos(n\theta_3) - ... + \cos(n\theta_m)] \cdot \sin(n\omega t) \quad (1)$$

Fourier expansion of (1) is rearranged to form a system of equations as illustrated in formula (2) below:

$$\begin{cases} \frac{4V_{dc}}{\pi}(\cos\theta_1 - \cos\theta_2 ... + \cos\theta_m) = V_{LF} \\ \cos3\theta_1 - \cos3\theta_2 ... + \cos3\theta_m = 0 \\ \cos5\theta_1 - \cos5\theta_2 ... + \cos5\theta_m = 0 \\ \cos k\theta_1 - \cos k\theta_2 ... + \cos k\theta_m = 0 \\ ... \\ \cos n\theta_1 - \cos n\theta_2 ... + \cos n\theta_m = 0 \end{cases} \quad (2)$$

In formula (2), $V_{LF}$ refers to the desired fundamental frequency as inverter output, and certain high order harmonics can be eliminated to the $n^{th}$ order. Solving formula (2) generates the switching angles, namely, pulses 400a, b, c, . . . n, for synthesizing the RF waveform 402 while eliminating undesired harmonics. In embodiments, two solver loops may be employed to solve the transcendental equations of formula (2).

With respect to the bipolar switching angle waveform 500, the following formulas (3) and (4) may be used as described above with respect to the unipolar switching angle waveform 400.

$$v(\omega t) = \sum_{n=1,3,5,...}^{\infty} \frac{4V_{dc}}{n\pi}[1 - 2\cos(n\theta_1) + 2\cos(n\theta_2) - 2\cos(n\theta_3) + ... + 2\cos(n\theta_m)] \cdot \sin(n\omega t) \quad (3)$$

-continued $$\begin{cases} \frac{4V_{dc}}{\pi}(1-2\cos\theta_1+2\cos\theta_2\ldots+2\cos\theta_m)=V_{LF} & (4) \\ 1-2\cos 3\theta_1+2\cos 3\theta_2\ldots+2\cos 3\theta_m=0 \\ 1-2\cos 5\theta_1+2\cos 5\theta_2\ldots+2\cos 5\theta_m=0 \\ 1-2\cos k\theta_1+2\cos k\theta_2\ldots+2\cos k\theta_m=0 \\ \quad\ldots \\ 1-2\cos n\theta_1+\cos n\theta_2\ldots+2\cos n\theta_m=0 \end{cases}$$

In traditional PWM modulation schemes, only a fundamental frequency waveform is generated and controlled, while unregulated harmonics are filtered. In the SHE modulation according to the present disclosure, however, both the fundamental frequency waveform, e.g., RF waveforms 400 and 500, and the kth harmonic waveforms, are simultaneously generated and accurately modulated, and undesired harmonics, namely, higher frequencies, are eliminated. As illustrated in FIGS. 8 and 9, the SHE modulation according to the present disclosure, allows for regulation of the waveform amplitude at all frequencies above the fundamental frequency to zero.

While several embodiments of the disclosure have been shown in the drawings and/or described herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical generator, comprising:
   a power supply configured to output a direct current (DC) waveform;
   an inverter coupled to the power supply, the inverter including a plurality of switching elements;
   a current source interposed between and in electrical communication with the power supply and the inverter; and
   a controller coupled to the inverter and configured to generate a switching angle waveform including a plurality of switching pulses, the controller further configured to modulate a switching frequency and a duty cycle per switching period of the plurality of switching pulses to activate the plurality of switching elements to generate a radio frequency waveform based on the DC waveform to minimize harmonics of the radio frequency waveform.

2. The electrosurgical generator according to claim 1, wherein the plurality of switching elements of the inverter includes four switching elements arranged in an H-bridge topology.

3. The electrosurgical generator according to claim 2, wherein each of the switching elements is a wide bandgap field effect transistor.

4. The electrosurgical generator according to claim 1, wherein the controller is further configured to generate five switching pulses per each half period of the radio frequency waveform.

5. The electrosurgical generator according to claim 1, wherein the switching angle waveform is a unipolar symmetrical waveform.

6. The electrosurgical generator according to claim 1, wherein the switching angle waveform is a bipolar symmetrical waveform.

7. An electrosurgical system, comprising:
   a electrosurgical generator including:
      a power supply configured to output a direct current (DC) waveform;
      an inverter coupled to the power supply, the inverter including a plurality of switching elements; and
      a controller coupled to the inverter and configured to independently control each of a fundamental frequency and harmonics thereof, wherein the controller is configured to generate a switching angle waveform including a plurality of switching pulses, the controller further configured to modulate a switching frequency and a duty cycle per switching period of the plurality of switching pulses to activate the plurality of switching elements to generate a radio frequency waveform based on the DC waveform and to minimize the harmonics of the fundamental frequency of the radio frequency waveform; and
   an electrosurgical instrument configured to couple to the inverter and to transmit the radio frequency waveform.

8. The electrosurgical system according to claim 7, wherein the plurality of switching elements of the inverter includes four switching elements arranged in an H-bridge topology.

9. The electrosurgical system according to claim 8, wherein each of the switching elements is a wide bandgap field effect transistor.

10. The electrosurgical system according to claim 7, wherein the controller is further configured to generate five switching pulses per each half period of the radio frequency waveform.

11. The electrosurgical system according to claim 7, wherein the switching angle waveform is a unipolar symmetrical waveform.

12. The electrosurgical system according to claim 7, wherein the switching angle waveform is a bipolar symmetrical waveform.

* * * * *